US012137967B2

(12) United States Patent
Adawi et al.

(10) Patent No.: US 12,137,967 B2
(45) Date of Patent: Nov. 12, 2024

(54) ACCURATE POSITIONING AND SHAPE VISUALIZATION OF BALLOON CATHETER ABLATION TAGS

(71) Applicant: Biosense Webster (Israel) Ltd., Yokneam (IL)

(72) Inventors: Eid Adawi, Tur'an (IL); Zvi Dekel, Zichron Yaakov (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 981 days.

(21) Appl. No.: 17/081,926

(22) Filed: Oct. 27, 2020

(65) Prior Publication Data

US 2021/0137588 A1     May 13, 2021

Related U.S. Application Data

(60) Provisional application No. 62/934,331, filed on Nov. 12, 2019.

(51) Int. Cl.
| | |
|---|---|
| *A61B 18/14* | (2006.01) |
| *A61B 18/00* | (2006.01) |
| *A61B 90/00* | (2016.01) |

(52) U.S. Cl.
CPC .......... *A61B 18/1492* (2013.01); *A61B 90/37* (2016.02); *A61B 90/39* (2016.02);
(Continued)

(58) Field of Classification Search
CPC ......... A61B 5/061; A61B 5/065; A61B 5/066; A61B 34/10; A61B 34/20; A61B 2034/104; A61B 2034/102; A61B 2034/2063
See application file for complete search history.

(56) References Cited

U.S. PATENT DOCUMENTS

| | | |
|---|---|---|
| D123,782 S | 12/1940 | Paul |
| 3,316,896 A | 5/1967 | Louis |
| | (Continued) | |

FOREIGN PATENT DOCUMENTS

| | | |
|---|---|---|
| CN | 101422637 A | 5/2009 |
| CN | 102271607 A | 12/2011 |
| | (Continued) | |

OTHER PUBLICATIONS

Extended European Search Report issued in European Patent Application No. 20 20 6844 dated Mar. 16, 2021.
(Continued)

*Primary Examiner* — Ronald Hupczey, Jr.
(74) *Attorney, Agent, or Firm* — Troutman Pepper Hamilton Sanders LLP (57) ABSTRACT

Embodiments of the present invention include generating a 3D model of a body cavity, and receiving, from a position transducer associated with a medical probe configured to be inserted into the cavity and having at least one elongated electrode disposed along a distal end of the probe, signals indicating orientation and location coordinates of the distal end within the body cavity. Based on the model and the signals, while parts of the given electrode other than the identified segment are not in contact with the inner surface of the cavity, a segment along a length of a given electrode that is in contact with tissue at a site on an inner surface of the cavity is identified. A graphical representation of the model with a visual marker at a location on the model corresponding to the site contacted by the segment of the given electrode is rendered to a display.

20 Claims, 8 Drawing Sheets

(52) U.S. Cl.
CPC .............. *A61B 2018/0022* (2013.01); *A61B 2018/00351* (2013.01); *A61B 2018/00577* (2013.01); *A61B 2018/00982* (2013.01); *A61B 2090/374* (2016.02); *A61B 2090/3762* (2016.02); *A61B 2090/378* (2016.02); *A61B 2090/3937* (2016.02)

(56) References Cited

U.S. PATENT DOCUMENTS

| | | |
|---|---|---|
| 4,276,874 A | 7/1981 | Wolvek et al. |
| 4,587,975 A | 5/1986 | Salo et al. |
| 4,709,698 A | 12/1987 | Johnston et al. |
| 4,805,621 A | 2/1989 | Heinze et al. |
| 5,178,957 A | 1/1993 | Kolpe et al. |
| 5,391,199 A | 2/1995 | Ben-Haim |
| 5,429,617 A | 7/1995 | Hammersmark et al. |
| 5,443,489 A | 8/1995 | Ben-Haim |
| 5,558,091 A | 9/1996 | Acker et al. |
| 5,582,609 A | 12/1996 | Swanson et al. |
| 5,584,830 A | 12/1996 | Ladd et al. |
| 5,702,386 A | 12/1997 | Stern et al. |
| 5,718,241 A | 2/1998 | Ben-Haim et al. |
| 5,797,903 A | 8/1998 | Swanson et al. |
| 5,860,974 A | 1/1999 | Abele |
| 5,944,022 A | 8/1999 | Nardella et al. |
| 5,971,983 A | 10/1999 | Lesh |
| 5,983,126 A | 11/1999 | Wittkampf |
| 6,012,457 A | 1/2000 | Lesh |
| 6,024,740 A | 2/2000 | Lesh et al. |
| 6,042,580 A | 3/2000 | Simpson |
| 6,123,718 A | 9/2000 | Tu et al. |
| 6,164,283 A | 12/2000 | Lesh |
| 6,171,275 B1 | 1/2001 | Webster, Jr. |
| 6,172,499 B1 | 1/2001 | Ashe |
| 6,176,832 B1 | 1/2001 | Habu et al. |
| 6,177,792 B1 | 1/2001 | Govari et al. |
| 6,198,974 B1 | 3/2001 | Webster, Jr. |
| 6,226,542 B1 | 5/2001 | Reisfeld |
| 6,301,496 B1 | 10/2001 | Reisfeld |
| 6,322,558 B1 | 11/2001 | Taylor et al. |
| 6,380,957 B1 | 4/2002 | Banning |
| 6,402,740 B1 | 6/2002 | Ellis et al. |
| D462,389 S | 9/2002 | Provence et al. |
| 6,456,864 B1 | 9/2002 | Swanson et al. |
| 6,471,693 B1 | 10/2002 | Carroll et al. |
| 6,514,249 B1 | 2/2003 | Maguire et al. |
| 6,522,930 B1 | 2/2003 | Schaer et al. |
| 6,656,174 B1 | 12/2003 | Hegde et al. |
| 6,788,967 B2 | 9/2004 | Ben-Haim et al. |
| 6,814,733 B2 | 11/2004 | Schwartz et al. |
| 6,893,433 B2 | 5/2005 | Lentz |
| 6,986,744 B1 | 1/2006 | Krivitski |
| 6,987,995 B2 | 1/2006 | Drysen |
| 6,997,924 B2 | 2/2006 | Schwartz et al. |
| 7,142,903 B2 | 11/2006 | Rodriguez et al. |
| 7,156,816 B2 | 1/2007 | Schwartz et al. |
| 7,274,957 B2 | 9/2007 | Drysen |
| 7,340,307 B2 | 3/2008 | Maguire et al. |
| 7,377,906 B2 | 5/2008 | Selkee |
| 7,442,190 B2 | 10/2008 | Abbound et al. |
| 7,536,218 B2 | 5/2009 | Govari et al. |
| 7,591,799 B2 | 9/2009 | Selkee |
| 7,593,760 B2 | 9/2009 | Rodriguez et al. |
| 7,720,517 B2 | 5/2010 | Drysen |
| 7,756,576 B2 | 7/2010 | Levin |
| 7,842,031 B2 | 11/2010 | Abboud et al. |
| 7,853,302 B2 | 12/2010 | Rodriguez et al. |
| 8,000,765 B2 | 8/2011 | Rodriguez et al. |
| 8,021,327 B2 | 9/2011 | Selkee |
| 8,048,032 B2 | 11/2011 | Root et al. |
| 8,231,617 B2 | 7/2012 | Satake |
| 8,267,932 B2 | 9/2012 | Baxter et al. |
| 8,275,440 B2 | 9/2012 | Rodriguez et al. |
| 8,348,888 B2 | 1/2013 | Selkee |
| 8,357,152 B2 | 1/2013 | Govari et al. |
| D682,289 S | 5/2013 | Dijulio et al. |
| D682,291 S | 5/2013 | Baek et al. |
| D690,318 S | 9/2013 | Kluttz et al. |
| D694,652 S | 12/2013 | Tompkin |
| 8,641,709 B2 | 2/2014 | Sauvageau et al. |
| 8,721,590 B2 | 5/2014 | Seward et al. |
| 8,777,161 B2 | 7/2014 | Pollock et al. |
| D716,340 S | 10/2014 | Bresin et al. |
| 8,852,181 B2 | 10/2014 | Malecki et al. |
| D720,766 S | 1/2015 | Mandal et al. |
| D721,379 S | 1/2015 | Moon et al. |
| D724,618 S | 3/2015 | Shin |
| 8,998,893 B2 | 4/2015 | Avitall |
| D729,263 S | 5/2015 | Ahn et al. |
| 9,089,350 B2 | 7/2015 | Willard |
| D736,780 S | 8/2015 | Wang |
| 9,126,023 B1 | 9/2015 | Sahatjian et al. |
| D740,308 S | 10/2015 | Kim et al. |
| D743,424 S | 11/2015 | Danielyan et al. |
| D744,000 S | 11/2015 | Villamor et al. |
| 9,173,758 B2 | 11/2015 | Brister et al. |
| D747,742 S | 1/2016 | Fan et al. |
| D750,644 S | 3/2016 | Bhutani et al. |
| 9,283,034 B2 | 3/2016 | Katoh et al. |
| 9,289,141 B2 | 3/2016 | Lowery et al. |
| D753,690 S | 4/2016 | Vazquez et al. |
| 9,320,631 B2 | 4/2016 | Moore et al. |
| 9,345,540 B2 | 5/2016 | Mallin et al. |
| D759,673 S | 6/2016 | Looney et al. |
| D759,675 S | 6/2016 | Looney et al. |
| D764,500 S | 8/2016 | Wang |
| D765,709 S | 9/2016 | Gagnier |
| D767,616 S | 9/2016 | Jones et al. |
| D768,696 S | 10/2016 | Gagnier |
| D783,037 S | 4/2017 | Hariharan et al. |
| 9,655,677 B2 | 5/2017 | Salahieh et al. |
| D791,805 S | 7/2017 | Segars |
| 9,795,442 B2 | 10/2017 | Salahieh et al. |
| 9,907,610 B2 | 3/2018 | Beeckler et al. |
| 9,956,035 B2 | 5/2018 | Govari et al. |
| 10,413,185 B1 | 9/2019 | Boveja et al. |
| D861,717 S | 10/2019 | Brekke et al. |
| 10,688,278 B2 | 6/2020 | Beeckler et al. |
| 10,751,121 B2 | 8/2020 | Govari et al. |
| 2001/0031961 A1 | 10/2001 | Hooven |
| 2002/0002369 A1 | 1/2002 | Hood |
| 2002/0065455 A1 | 5/2002 | Ben-Haim et al. |
| 2002/0068931 A1 | 6/2002 | Wong et al. |
| 2002/0077627 A1 | 6/2002 | Johnson et al. |
| 2002/0160134 A1 | 10/2002 | Ogushi et al. |
| 2003/0018327 A1 | 1/2003 | Truckai et al. |
| 2003/0028183 A1 | 2/2003 | Sanchez et al. |
| 2003/0050637 A1 | 3/2003 | Maguire et al. |
| 2003/0060820 A1 | 3/2003 | Maguire et al. |
| 2003/0144658 A1 | 7/2003 | Schwartz et al. |
| 2004/0122445 A1 | 6/2004 | Butler et al. |
| 2004/0147920 A1 | 7/2004 | Keidar |
| 2004/0225285 A1 | 11/2004 | Gibson |
| 2005/0070887 A1 | 3/2005 | Taimisto et al. |
| 2005/0119686 A1 | 6/2005 | Clubb |
| 2006/0013595 A1 | 1/2006 | Trezza et al. |
| 2006/0106375 A1 | 5/2006 | Werneth et al. |
| 2006/0135953 A1 | 6/2006 | Kania et al. |
| 2007/0071792 A1 | 3/2007 | Varner et al. |
| 2007/0080322 A1 | 4/2007 | Walba |
| 2007/0083194 A1 | 4/2007 | Kunis et al. |
| 2007/0287994 A1 | 12/2007 | Patel |
| 2008/0009700 A1* | 1/2008 | Dumoulin .............. A61B 5/055 600/410 |
| 2008/0018891 A1 | 1/2008 | Hell et al. |
| 2008/0021313 A1 | 1/2008 | Eidenschink et al. |
| 2008/0051707 A1 | 2/2008 | Phan et al. |
| 2008/0140072 A1 | 6/2008 | Stangenes et al. |
| 2008/0183132 A1 | 7/2008 | Davies et al. |
| 2008/0188912 A1 | 8/2008 | Stone et al. |
| 2008/0202637 A1 | 8/2008 | Hector et al. |
| 2008/0208186 A1 | 8/2008 | Slater |
| 2008/0249463 A1 | 10/2008 | Pappone et al. |
| 2008/0262489 A1 | 10/2008 | Steinke |

(56) References Cited

U.S. PATENT DOCUMENTS

| | | |
|---|---|---|
| 2008/0275300 A1 | 11/2008 | Rothe et al. |
| 2008/0281312 A1 | 11/2008 | Werneth et al. |
| 2009/0163890 A1 | 6/2009 | Clifford et al. |
| 2009/0182318 A1 | 7/2009 | Abboud et al. |
| 2009/0270850 A1 | 10/2009 | Zhou et al. |
| 2010/0069836 A1 | 3/2010 | Satake |
| 2010/0114269 A1 | 5/2010 | Wittenberger et al. |
| 2010/0204560 A1 | 8/2010 | Salahieh et al. |
| 2010/0256629 A1 | 10/2010 | Wylie et al. |
| 2010/0324552 A1 | 12/2010 | Kauphusman et al. |
| 2011/0118632 A1 | 5/2011 | Sinelnikov et al. |
| 2011/0130648 A1 | 6/2011 | Beeckler et al. |
| 2011/0282338 A1 | 11/2011 | Fojtik |
| 2011/0295248 A1 | 12/2011 | Wallace et al. |
| 2011/0301587 A1 | 12/2011 | Deem et al. |
| 2011/0313286 A1 | 12/2011 | Whayne et al. |
| 2012/0019107 A1 | 1/2012 | Gabl et al. |
| 2012/0029511 A1 | 2/2012 | Smith et al. |
| 2012/0065503 A1 | 3/2012 | Rogers et al. |
| 2012/0071870 A1 | 3/2012 | Salahieh et al. |
| 2012/0079427 A1 | 3/2012 | Carmichael et al. |
| 2012/0101413 A1 | 4/2012 | Beetel et al. |
| 2012/0101538 A1 | 4/2012 | Ballakur et al. |
| 2012/0143177 A1 | 6/2012 | Avitall |
| 2012/0143293 A1 | 6/2012 | Mauch et al. |
| 2012/0191079 A1 | 7/2012 | Moll et al. |
| 2012/0209260 A1 | 8/2012 | Lambert et al. |
| 2013/0085360 A1 | 4/2013 | Grunewald |
| 2013/0090649 A1 | 4/2013 | Smith et al. |
| 2013/0109982 A1 | 5/2013 | Sato et al. |
| 2013/0116550 A1 | 5/2013 | Ishii et al. |
| 2013/0150693 A1 | 6/2013 | D'Angelo et al. |
| 2013/0165916 A1 | 6/2013 | Mathur et al. |
| 2013/0165941 A1 | 6/2013 | Murphy |
| 2013/0165990 A1 | 6/2013 | Mathur et al. |
| 2013/0169624 A1 | 7/2013 | Bourier et al. |
| 2013/0261692 A1 | 10/2013 | Cardinal et al. |
| 2013/0274562 A1 | 10/2013 | Ghaffari et al. |
| 2013/0274658 A1 | 10/2013 | Steinke et al. |
| 2013/0282084 A1 | 10/2013 | Mathur et al. |
| 2013/0318439 A1 | 11/2013 | Landis et al. |
| 2014/0012242 A1 | 1/2014 | Lee et al. |
| 2014/0018788 A1 | 1/2014 | Engelman et al. |
| 2014/0031813 A1 | 1/2014 | Tellio et al. |
| 2014/0058197 A1 | 2/2014 | Salahieh et al. |
| 2014/0121470 A1 | 5/2014 | Scharf et al. |
| 2014/0148805 A1 | 5/2014 | Stewart et al. |
| 2014/0227437 A1 | 8/2014 | Deboer et al. |
| 2014/0243821 A1 | 8/2014 | Salahieh et al. |
| 2014/0275993 A1 | 9/2014 | Ballakur |
| 2014/0276756 A1 | 9/2014 | Hill |
| 2014/0276811 A1 | 9/2014 | Koblish et al. |
| 2014/0288546 A1 | 9/2014 | Sherman et al. |
| 2014/0330266 A1 | 11/2014 | Thompson et al. |
| 2014/0357956 A1 | 12/2014 | Salahieh et al. |
| 2015/0005799 A1 | 1/2015 | Lindquist et al. |
| 2015/0025532 A1 | 1/2015 | Hanson et al. |
| 2015/0025533 A1 | 1/2015 | Groff et al. |
| 2015/0057655 A1 | 2/2015 | Osypka |
| 2015/0067512 A1 | 3/2015 | Roswell |
| 2015/0080883 A1 | 3/2015 | Haverkost et al. |
| 2015/0105774 A1 | 4/2015 | Lindquist et al. |
| 2015/0112256 A1 | 4/2015 | Byrne et al. |
| 2015/0112321 A1 | 4/2015 | Cadouri |
| 2015/0119875 A1 | 4/2015 | Fischell et al. |
| 2015/0141982 A1 | 5/2015 | Lee |
| 2015/0157382 A1 | 6/2015 | Avitall et al. |
| 2015/0216591 A1 | 8/2015 | Cao et al. |
| 2015/0216650 A1 | 8/2015 | Shaltis |
| 2015/0265329 A1 | 9/2015 | Lalonde et al. |
| 2015/0265339 A1 | 9/2015 | Lindquist et al. |
| 2015/0265812 A1 | 9/2015 | Lalonde |
| 2015/0272667 A1 | 10/2015 | Govari et al. |
| 2015/0327805 A1 | 11/2015 | Ben-Haim |
| 2015/0341752 A1 | 11/2015 | Flynn |
| 2016/0000499 A1 | 1/2016 | Lennox et al. |
| 2016/0051321 A1 | 2/2016 | Salahieh et al. |
| 2016/0085431 A1 | 3/2016 | Kim et al. |
| 2016/0106499 A1 | 4/2016 | Ogata et al. |
| 2016/0166306 A1 | 6/2016 | Pageard |
| 2016/0175041 A1 | 6/2016 | Govari et al. |
| 2016/0196635 A1 | 7/2016 | Cho et al. |
| 2016/0256305 A1 | 9/2016 | Longo et al. |
| 2016/0374748 A9 | 12/2016 | Salahieh et al. |
| 2017/0042614 A1 | 2/2017 | Salahieh et al. |
| 2017/0042615 A1 | 2/2017 | Salahieh et al. |
| 2017/0080192 A1 | 3/2017 | Giasolli et al. |
| 2017/0143359 A1 | 5/2017 | Nguyen et al. |
| 2017/0164464 A1 | 6/2017 | Weinkam et al. |
| 2017/0311829 A1 | 11/2017 | Beeckler et al. |
| 2017/0311893 A1 | 11/2017 | Beeckler et al. |
| 2017/0312022 A1 | 11/2017 | Beeckler et al. |
| 2017/0347896 A1 | 12/2017 | Keyes et al. |
| 2018/0064495 A1* | 3/2018 | Hareland ............... A61B 34/20 |
| 2018/0074693 A1 | 3/2018 | Jones et al. |
| 2018/0110562 A1 | 4/2018 | Govari et al. |
| 2018/0125575 A1 | 5/2018 | Schwartz et al. |
| 2018/0256247 A1 | 9/2018 | Govari et al. |
| 2018/0280080 A1 | 10/2018 | Govari et al. |
| 2018/0333162 A1 | 11/2018 | Saab |
| 2018/0368927 A1 | 12/2018 | Lyons et al. |
| 2019/0059818 A1 | 2/2019 | Herrera et al. |
| 2019/0060622 A1 | 2/2019 | Beeckler |
| 2019/0143079 A1 | 5/2019 | Beeckler et al. |
| 2019/0175262 A1 | 6/2019 | Govari et al. |
| 2019/0175263 A1 | 6/2019 | Altmann et al. |
| 2019/0183567 A1 | 6/2019 | Govari et al. |
| 2019/0201669 A1 | 7/2019 | Govari et al. |
| 2019/0217065 A1 | 7/2019 | Govari et al. |
| 2019/0297441 A1 | 9/2019 | Dehe et al. |
| 2019/0298441 A1 | 10/2019 | Clark et al. |
| 2019/0365451 A1 | 12/2019 | Jung, Jr. |
| 2020/0001054 A1 | 1/2020 | Jimenez et al. |
| 2020/0015693 A1 | 1/2020 | Beeckler et al. |
| 2020/0085497 A1 | 3/2020 | Zhang et al. |
| 2020/0155226 A1 | 5/2020 | Valls et al. |
| 2021/0169567 A1 | 6/2021 | Govari et al. |

FOREIGN PATENT DOCUMENTS

| | | |
|---|---|---|
| CN | 102458566 A | 5/2012 |
| CN | 203539434 U | 4/2014 |
| CN | 104244856 A | 12/2014 |
| CN | 104546117 A | 4/2015 |
| CN | 105105844 A | 12/2015 |
| CN | 105473091 A | 4/2016 |
| CN | 105473093 A | 4/2016 |
| EP | 0779059 A1 | 6/1997 |
| EP | 1790304 A2 | 5/2007 |
| EP | 2749214 A1 | 7/2014 |
| EP | 2865350 A2 | 4/2015 |
| EP | 2875790 A2 | 5/2015 |
| EP | 3238646 A2 | 11/2017 |
| EP | 3238648 A1 | 11/2017 |
| EP | 3251622 A1 | 12/2017 |
| EP | 3300680 A1 | 4/2018 |
| EP | 3315087 A1 | 5/2018 |
| EP | 3332727 A2 | 6/2018 |
| EP | 3 372 276 A1 | 9/2018 |
| EP | 3 384 852 A1 | 10/2018 |
| EP | 3571983 A2 | 11/2019 |
| EP | 3586778 A1 | 1/2020 |
| EP | 3653153 A1 | 5/2020 |
| JP | H06261951 A | 9/1994 |
| JP | H1176233 A | 3/1999 |
| JP | 2000504242 A | 4/2000 |
| JP | 2005052424 A | 3/2005 |
| JP | 2010507404 A | 3/2010 |
| JP | 2012024156 A | 2/2012 |
| JP | 2013013726 A | 1/2013 |
| JP | 2013031655 A | 2/2013 |
| JP | 2013078587 A | 5/2013 |
| JP | 2013529109 A | 7/2013 |
| JP | 2014529419 A | 11/2014 |

(56) References Cited

FOREIGN PATENT DOCUMENTS

| | | |
|---|---|---|
| JP | 2015503365 A | 2/2015 |
| JP | 2015100706 A | 6/2015 |
| JP | 2015112113 A | 6/2015 |
| JP | 2015112114 A | 6/2015 |
| JP | 2015518776 A | 7/2015 |
| JP | 2016515442 A | 5/2016 |
| JP | 2016116863 A | 6/2016 |
| JP | 2019034119 A | 3/2019 |
| WO | 0056237 A2 | 9/2000 |
| WO | 02102231 A2 | 12/2002 |
| WO | 2005041748 A2 | 5/2005 |
| WO | 2008049087 A2 | 4/2008 |
| WO | 2011143468 A2 | 11/2011 |
| WO | 2013049601 A2 | 4/2013 |
| WO | 2013052919 A2 | 4/2013 |
| WO | 2013154776 A2 | 10/2013 |
| WO | 2014168987 A1 | 10/2014 |
| WO | 2015049784 A1 | 4/2015 |
| WO | 2016183337 A2 | 11/2016 |
| WO | 2016210437 A1 | 12/2016 |
| WO | 2017024306 A1 | 2/2017 |
| WO | 2017087549 A1 | 5/2017 |
| WO | 2018106569 A1 | 6/2018 |
| WO | 2018129133 A1 | 7/2018 |
| WO | 2019095020 A1 | 5/2019 |

OTHER PUBLICATIONS

Angela O., "AF Symposium 2017: First-in-Man Study Shows Promising Results with a Multi-Electrode Radiofrequency Balloon for Paroxysmal AF Treatment," Cardiac Rhythm News, Jan. 20, 2017, 2 Pages, [Retrieved on Dec. 16, 2020] Retrieved from URL: https://cardiacrhythmnews.com/fist-in-man-study-shows-promising-results-with-a-multi-electrode-radiofrequency-balloon-for-paroxysmal-af-treatment/.

Casella M., et al., "Ablation Index as a Predictor of Long-Term Efficacy in Premature Ventricular Complex Ablation: A Regional Target Value Analysis," Heart Rhythm Society, Jun. 2019, vol. 16, No. 6, pp. 888-895.

Co-Pending U.S. Appl. No. 14/578,807, filed Dec. 22, 2014, 21 pages.

Das M., et al., "Ablation Index, a Novel Marker of Ablation Lesion Quality: Prediction of Pulmonary Vein Reconnection at Repeat Electrophysiology Study and Regional Differences in Target Values," Europace, 2017, Published Online May 31, 2016, vol. 19, pp. 775-783.

Dorobantu M., et al., "Oral Anticoagulation During Atrial Fibrillation Ablation: Facts and Controversies," Cor et Vasa, 2013, Accepted on Dec. 3, 2012, vol. 55, No. 2, pp. e101-e106, Retrieved from URL: https://www.sciencedirect.com/science/article/pii/S0010865012001415.

Extended European Search Report for Application No. EP17168513.4 mailed Sep. 18, 2017, 11 pages.

Extended European Search Report for European Application No. 15201723.2, mailed May 11, 2016, 07 Pages.

Extended European Search Report for European Application No. 17168393.1 mailed Dec. 15, 2017, 12 Pages.

Extended European Search Report for European Application No. 17168518.3, mailed Sep. 20, 2017, 9 Pages.

Extended European Search Report for European Application No. 17173893.3, mailed Nov. 6, 2017, 8 Pages.

Extended European Search Report for European Application No. 17201434.2, mailed Feb. 1, 2018, 10 Pages.

Extended European Search Report for European Application No. 17205876.0, mailed Jun. 1, 2018, 13 Pages.

Extended European Search Report for European Application No. 19177365.4, mailed Nov. 8, 2019, 07 Pages.

Extended European Search Report for European Application No. 19183327.6, mailed Nov. 21, 2019, 8 Pages.

Extended European Search Report for European Application No. 20153872.5, mailed May 7, 2020, 9 Pages.

Extended European Search Report for European Application No. 20195648.9, mailed Feb. 12, 2021, 8 Pages.

Fornell D., "Multi-Electrode RF Balloon Efficient for Acute Pulmonary Vein Isolation," Diagnostic and Interventional Cardiology, May 17, 2017, 3 Pages, [Retrieved on Dec. 16, 2020] Retrieved from URL: www.dicardiology.com/article/multi-electrode-rf-balloon-efficient-acute-pulmonary-vein-isolation.

Haines D.E., et al., "The Promise of Pulsed Field Ablation," Dec. 2019, vol. 19, No. 12, 10 pages.

Honarbakhsh S., et al., "Radiofrequency Balloon Catheter Ablation for Paroxysmal Atrial Fibrillation, Radiance Study—a UK experience," EP Europace, Oct. 2017, vol. 19, No. 1, p. i21, 3 Pages.

International Search Report and Written Opinion for International Application No. PCT/IB2019/052313, mailed Jul. 22, 2019, 8 Pages.

International Search Report and Written Opinion for International Application No. PCT/IB2019/056381, mailed Dec. 17, 2019, 10 pages.

International Search Report and Written Opinion for International Application No. PCT/IB2019/057743, mailed Dec. 6, 2019, 16 Pages.

International Search Report and Written Opinion issued in corresponding International Application No. PCT/IB2019/057742, dated Nov. 28, 2019, 18 Pages.

Nagashima K., et al., "Hot Balloon Versus Cryoballoon Ablation for Atrial Fibrillation," Circulation: Arrhythmia and Electrophysiology, May 2018, vol. 11, No. 5, e005861, 9 Pages.

Napoli N., et al., "For Atrial Fibrillation Ablation, Newer Anticoagulant Reduces Major Bleeds," American College of Cardiology, Mar. 19, 2017, 4 Pages, [Retrieved on Jan. 21, 2022] Retrieved from URL: https://www.acc.org/about-acc/press-releases/2017/03/18/08/47/sun-1045am-for-atrial-fibrillation-ablation-newer-anticoagulant-reduces-major-bleeds.

Okano T., et al., "Wire Perforation Causing Cardiopulmonary Arrest During Radiofrequency Hot Balloon Ablation for Pulmonary Vein Isolation," Journal of Cardiology Cases, Feb. 15, 2019, vol. 19, No. 5, pp. 169-172.

Partial European Search Report for European Application No. 17168393.1 mailed Sep. 13, 2017, 13 Pages.

Partial European Search Report for European Application No. 17205876.0, mailed Feb. 22, 2018, 10 Pages.

Reddy V.Y., et al., "Balloon Catheter Ablation to Treat Paroxysmal Atrial Fibrillation: What is the Level of Pulmonary Venous Isolation?," Heart Rhythm, Mar. 2008, vol. 5, No. 3, pp. 353-360, 3 Pages.

Winkle R.A., et al., "Atrial Fibrillation Ablation Using Open-Irrigated Tip Radiofrequency: Experience with Intraprocedural Activated Clotting Times ≤ 210 Seconds," Heart Rhythm, Jun. 2014, Epub Mar. 27, 2014, vol. 11, No. 6, pp. 963-968.

Youtube:, "Intensity™ CX4 Professional E-Stim/ Ultrasound Combo," Dec. 22, 2015, 1 Page, [Retrieved on Nov. 19, 2020], Retrieved from URL: https://www.youtube.com/watch?v=76s1QKMWJME].

Youtube: "New Interface TactiCath Contact Force Ablation Catheter," Nov. 26, 2013, 1 Pages, [Retrieved on Nov. 19, 2020], Retrieved from URL: https: /Avww.youtube.com/watch?v=aYvYO8Hpylg].

Search Reported (English translation) dated Mar. 15, 2024, from corresponding Japanese Application No. 2020-187849.

Notice of Reasons for Refusal (English translation) dated Mar. 19, 2024, from corresponding Japanese Application No. 2020-187849.

Decision to Grant Patent (English translation) dated Jul. 2, 2024, from corresponding Japanese Application No. 2020-187849.

* cited by examiner

ACCURATE POSITIONING AND SHAPE VISUALIZATION OF BALLOON CATHETER ABLATION TAGS

PRIORITY

This application claims the benefits of priority under the Paris Convention as well as 35 USC § 119 from earlier filed U.S. Provisional Patent Application Ser. No. 62/934,331 filed on Nov. 12, 2019, titled "Accurate Positioning and Shape Visualization of Balloon Catheter Ablation Tags" which is hereby incorporated by reference as if set forth verbatim.

FIELD OF THE INVENTION

The present invention relates generally to medical imaging, and specifically to visualizing an area of tissue in contact with an ablation electrode.

BACKGROUND OF THE INVENTION

Arrhythmias are abnormal heart rhythms that are typically caused by a small area of cardiac tissue that produces irregular heartbeats. Cardiac ablation is a medical procedure that can be performed to treat an arrhythmia by destroying the area of the cardiac tissue causing the irregular heartbeats.

In some instances, cardiac ablation can be performed using a balloon catheter. A balloon catheter comprises an inflatable balloon at its distal end that can be inflated and deflated as necessary. The balloon typically comprises multiple electrodes configured to deliver ablation energy to tissue in contact with the electrodes. The balloon is typically deflated while the catheter is inserted into a body cavity (e.g., a heart) of a patient, inflated in order to perform the necessary procedure, and deflated again upon completing the procedure.

U.S. Pat. No. 6,514,249 to Maguire et al., describes a positioning system for orienting an ablation element within a pulmonary vein ostium. The system includes a position monitoring assembly that can be used to position a circumferential ablation member along a circumferential region of tissue at a location where a pulmonary vein extends from a left atrium.

U.S. Patent Application 2008/0275300 to Rothe et al., describes a complex shape steerable tissue visualization and manipulation catheter. The catheter includes a steering mechanism that can adjust a position of a visualization hood or membrane through which underlying tissue may be visualized.

The description above is presented as a general overview of related art in this field and should not be construed as an admission that any of the information it contains constitutes prior art against the present patent application.

SUMMARY OF THE INVENTION

There is provided, in accordance with an embodiment of the present invention, an apparatus including an invasive medical probe configured to be inserted into a body cavity and including a distal end having at least one elongated electrode disposed along the distal end, a position transducer associated with the medical probe, a memory configured to store a three-dimensional (3D) model of the body cavity, a display, and a processor configured to receive, from the position transducer, signals indicative of orientation and location coordinates of the distal end within the body cavity, to identify, based on the 3D model and the signals, a segment along a length of a given elongated electrode that is in contact with tissue at a site on an inner surface of the body cavity, while parts of the given elongated electrode other than the identified segment are not in contact with the inner surface of the body cavity, and to render to the display a graphical representation of the 3D model with a visual marker at a location on the 3D model corresponding to the site contacted by the segment of the given elongated electrode.

In some embodiments, the at least one elongated electrode is disposed longitudinally along the distal end of the medical probe.

In an additional embodiment, the invasive medical probe may also include an inflatable balloon that extends from a lumen in the distal end of the medical probe. In one embodiment, the at least one elongated electrode is disposed longitudinally on a surface of the balloon.

In another embodiment, the apparatus may also include an ablation module configured to deliver ablation energy to the at least one elongated electrode, thereby ablating the tissue that is in contact with the at least one electrode. In one embodiment, the visual marker corresponds to the site ablated by the segment of the given elongated electrode.

In a supplemental embodiment, processor can be configured, to receive, prior to receiving the signals, 3D model data for the body cavity, and to generate, using the 3D model data, the 3D model. In some embodiments, wherein the 3D model data can be selected from a list consisting of anatomical mapping data, computed tomography data, magnetic resonance imaging data and ultrasound data.

In a further embodiment, the processor can be configured to determine, based on the 3D model and the signals, an engagement contour of the segment along the length of the given elongated electrode that is in contact with the tissue, and wherein the processor is configured to render the visual marker at a location on the 3D model by presenting, at the location on the 3D model, a visual marker contour corresponding to the engagement contour.

There is also provided, in accordance with an embodiment of the present invention, a method including generating a three-dimensional (3D) model of a body cavity, receiving, from a position transducer associated with a medical probe configured to be inserted into the body cavity and including a distal end having at least one elongated electrode disposed along the distal end, signals indicative of orientation and location coordinates of the distal end within the body cavity, identifying, based on the 3D model and the signals, a segment along a length of a given elongated electrode that is in contact with tissue at a site on an inner surface of the body cavity, while parts of the given elongated electrode other than the identified segment are not in contact with the inner surface of the body cavity, and rendering to the display a graphical representation of the 3D model with a visual marker at a location on the 3D model corresponding to the site contacted by the segment of the given elongated electrode.

There is further provided, in accordance with an embodiment of the present invention, a computer software product operated in conjunction with a medical probe configured to be inserted into a body cavity and including a distal end having at least one elongated electrode disposed along the distal end, the product including a non-transitory computer-readable medium, in which program instructions are stored, which instructions, when read by a computer, cause the computer to generate a three-dimensional (3D) model of a body cavity, to receive, from a position transducer associated with the medical probe, signals indicative of orientation and location coordinates of the distal end within the body cavity, to identify, based on the 3D model and the signals, a segment along a length of a given elongated electrode that is in contact with tissue at a site on an inner surface of the body cavity, while parts of the given elongated electrode other than the identified segment are not in contact with the inner surface of the body cavity, and to render to the display a graphical representation of the 3D model with a visual marker at a location on the 3D model corresponding to the site contacted by the segment of the given elongated electrode.

BRIEF DESCRIPTION OF THE DRAWINGS

The disclosure is herein described, by way of example only, with reference to the accompanying drawings, wherein.

DETAILED DESCRIPTION OF EMBODIMENTS

Overview

Embodiments of the present invention describe a system and a method for presenting visual markers indicating areas of tissue being treated during a medical procedure such as cardiac ablation. As described hereinbelow, the system comprises an invasive medical probe configured to be inserted into a body cavity and comprising a distal end having at least one elongated electrode disposed along the distal end. For example, the medical probe may comprise an intracardiac catheter having a balloon affixed to the distal end, wherein the one or more elongated electrodes are mounted on an outer surface of the balloon The system also comprises a position transducer associated with the medical probe. In some embodiments, as described hereinbelow, the position transducer may comprise a magnetic field sensor affixed to the distal end of the medical probe.

The system additionally comprises a display and a memory configured to store a three-dimensional (3D) model of the body cavity. In some embodiments, as described hereinbelow, the 3D model may be derived from an anatomical map, computerized tomography (CT) image data, magnetic resonance imaging (MRI) image data, or ultrasound image data.

The system further comprises a processor configured to receive, from the position transducer, signals indicative of orientation and location coordinates of the distal end within the body cavity, and to identify, based on the 3D model and the signals, a segment along a length of the elongated electrode that is in contact with tissue at a site on an inner surface of the body cavity, while parts of the elongated electrode other than the identified segment are not in contact with the inner surface of the body cavity. The processor is also configured to render to the display a graphical representation of the 3D model with a visual marker at a location on the 3D model corresponding to the site contacted by the segment of the elongated electrode.

By identifying respective segments of the elongated electrodes that are engaging tissue on the inner surface of the body cavity, systems implementing embodiments of the invention can aid a medical professional to accurately target areas of tissue for treatment. For example, if the elongated electrodes are configured to deliver ablation energy, systems implementing embodiments of the invention can accurately present the visual markers (e.g., ablation tags) that indicate locations in the tissue where the ablation energy is being delivered by the elongated electrodes during an ablation procedure.

System Description

Figure 1:
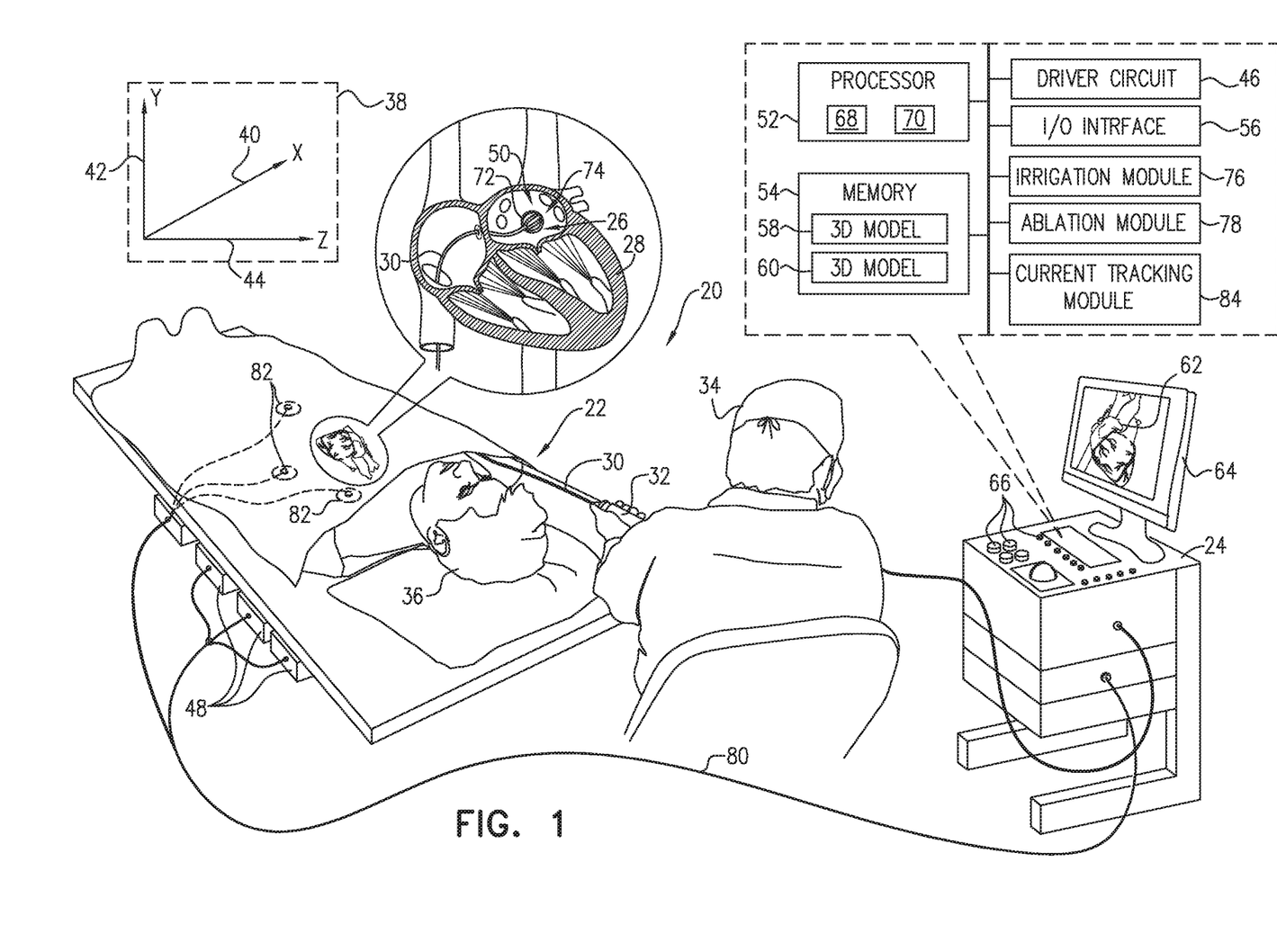
FIG. 1 is a schematic, pictorial illustration of a medical system comprising a medical console configured to generate a three-dimensional (3D) model of a body cavity, and a medical probe whose distal end comprises a balloon, in accordance with an embodiment of the present invention.
Figure 2:
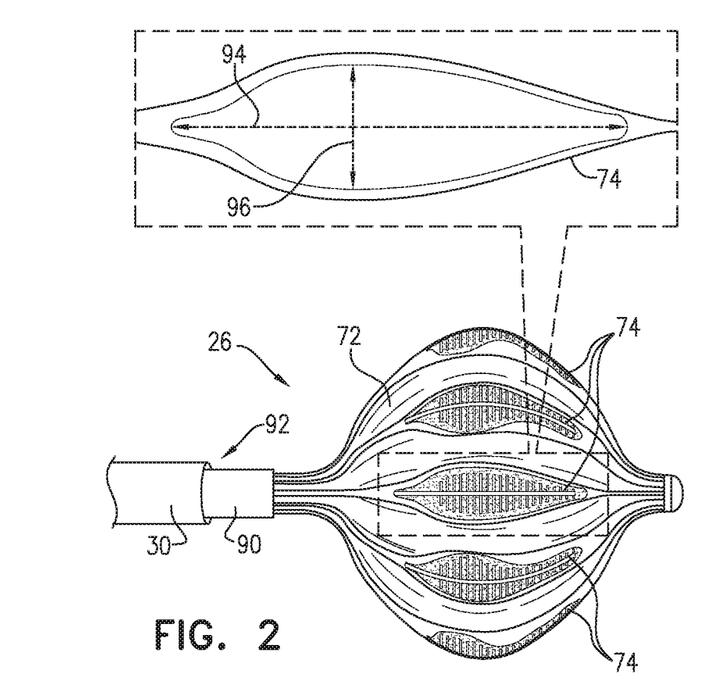
FIG. 2 is a schematic pictorial illustration of the distal end comprising multiple elongated electrodes mounted on the balloon, in accordance with an embodiment of the present invention.
Figure 3:
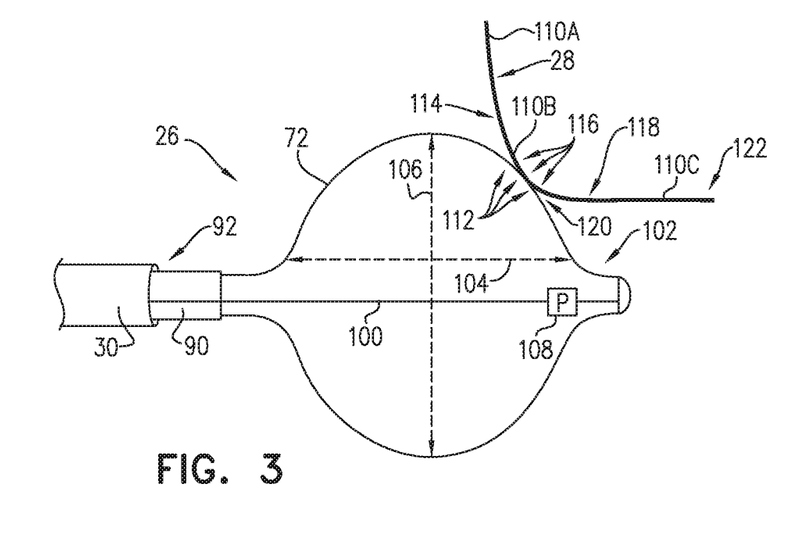
FIG. 3 is a schematic cutaway view of the distal end of the medical probe, in accordance with an embodiment of the present invention.

FIG. 1 is a schematic pictorial illustration of a medical system 20 comprising a medical probe 22 (e.g., an intracardiac catheter) and a control console 24, FIG. 2 is a schematic pictorial illustration of a distal end 26 of the medical probe, and FIG. 3 is a schematic cutaway view of the distal end 26, in accordance with an embodiment of the present invention. System 20 may be based, for example, on the CARTO® system, produced by Biosense Webster Inc. (33 Technology Drive, Irvine, CA 92618 USA). In embodiments described hereinbelow, it is assumed that probe 22 is used for diagnostic or therapeutic treatment, such as performing ablation of heart tissue in a heart 28. Alternatively, probe 22 may be used, mutatis mutandis, for other therapeutic and/or diagnostic purposes in the heart or in other body organs.

Probe 22 comprises an insertion tube 30 and a handle 32 coupled to a proximal end of the insertion tube. By manipulating handle 32, a medical professional 34 can insert probe 22 into a body cavity in a patient 36. For example, medical professional 34 can insert probe 22 through the vascular system of patient 36 so that distal end 26 of probe 22 enters a chamber of heart 28 and engages endocardial tissue at a desired location or locations.

In a first embodiment of the configuration shown in FIG. 1, system 20 uses magnetic position sensing to determine position coordinates indicate a location and an orientation of distal end 26 in a coordinate system 38 comprising an X-axis 40, a Y-axis 42 and a Z-axis 44. To implement magnetic based position sensing, control 24 comprises a driver circuit 46 which drives field generators 48 to generate magnetic fields within the body of patient 36. Typically, field generators 48 comprise coils, which are placed below the patient's torso at known positions external to patient 36. These coils generate magnetic fields in a predefined working volume that contains heart 28.

System 20 also comprises a position transducer 50 that is associated with medical probe 22, and a processor 52 in medical console 24. In embodiments described herein, position transducer 50 comprises a component of medical system 20 that generates and conveys position signals indicating a current position (i.e., location and orientation) of distal end 26, and processor 52 is configured to receive and process the conveyed position signals in order to compute, in coordinate system 38, orientation and location coordinates of distal end 26.

In the first embodiment of the configuration shown in FIG. 1, position transducer 50 comprises a magnetic field sensor within distal end 26 of probe 22. In this embodiment, the magnetic field sensor generates electrical signals in response to the magnetic fields from the coils, thereby enabling console to determine the position of distal end 26 within the chamber.

In this embodiment, system 20 measures the position of distal end 26 using magnetic-based sensors. Magnetic position tracking techniques are described, for example, in U.S. Pat. Nos. 5,391,199, 5,443,489, 6,788,967, 5,558,091, 6,172,499 and 6,177,792. The methods of location sensing described hereinabove are implemented in the above-mentioned CARTO® system and are described in detail in the patents cited above.

In addition to driver circuit 46 and processor 52, control console 24 also comprises a memory 54 and an input/output (I/O) communications interface 56. In embodiments described herein, memory 54 stores a 3D model 58 of heart 28 that processor 52 can generate based on 3D data such as anatomical mapping data received from a mapping catheter, computed tomography (CT) data, magnetic resonance imaging (MRI) data and ultrasound data. In some embodiments, memory 54 can also store a 3D model 60 of distal end 26, as described in the description referencing FIG. 8 hereinbelow.

In operation, I/O communications interface 56 enables control console 24 to receive signals from position transducer 50. Based on signals received from position transducer 50, processor 52 can process these signals in order to determine the position coordinates of distal end 26, typically comprising both location and orientation coordinates. As described in the description referencing FIG. 8 hereinbelow, processor 52 can update 3D model 58 based on the determined position coordinates.

During the procedure, processor 52 can present, to medical professional 34, a graphical representation 62 of 3D model 58 on a display 64. In some embodiments, medical professional 34 can manipulate graphical representation 62 using one or more input devices 66. In alternative embodiments, display 64 may comprise a touchscreen that can be configured to accept inputs from medical professional 34, in addition to presenting graphical representation 62.

Processor 52 may comprise real-time noise reduction circuitry 68 typically configured as a field programmable gate array (FPGA), followed by an analog-to-digital (A/D) signal conversion integrated circuit 70. The processor can be programmed to perform one or more algorithms disclosed herein, each of the one or more algorithms comprising steps described hereinbelow. The processor uses circuitry 68 and circuit 70 as well as features of modules which are described in more detail below, in order to perform the one or more algorithms.

Memory 54 may comprise any suitable volatile and/or non-volatile memory, such as random access memory, a solid-state drive or a hard disk drive.

Medical probe 22 comprises a balloon 72 having multiple elongated electrodes 74 that can be used to ablate tissue in a body cavity such as heart 28. Balloon 72 and electrodes 74 are described in the description referencing FIG. 2 hereinbelow.

Control console 24 further comprises an irrigation module that controls the inflation of balloon 72 and an ablation module 78 that controls the delivery of ablation energy to elongated electrodes 74.

In a second embodiment of the configuration shown in FIG. 1, medical system 20 may use impedance-based location sensing to determine location coordinates of distal end 26 in coordinate system 38. To implement impedance-based location sensing, control console 24 is connected, by a cable 80, to body surface electrodes, which typically comprise adhesive skin patches 82 that are affixed to patient 36. In the configuration shown in FIG. 1, cable 80 also connects field generators 48 to console 24.

Control console 24 also comprises a current tracking module that, in conjunction with processor 52, determines position coordinates of distal end 26 inside heart 28 based on impedances and/or currents measured between adhesive skin patches 82 and electrodes 74. When using impedance-based location sensing to determine location coordinates of distal end 26 in coordinate system 38, position transducer 50 may comprise a selected electrode 74 operating with adhesive patches 82.

Impedance-based and current-based position tracking techniques are described, for example, in U.S. Pat. Nos. 5,983,126, 6,456,864 and 5,944,022. The methods of position sensing described hereinabove are implemented in the above-mentioned CARTO® system and are described in detail in the patents cited above.

In operation, irrigation module 76 can use irrigation fluid to inflate balloon 72, and can control the inflation of the balloon by controlling a flow rate of the irrigation fluid into the balloon. Balloon 72 is typically formed from biocompatible material such as polyethylene terephthalate (PET), polyurethane, Nylon, or Pebax. In some embodiments, balloon 72 may comprise multiple small fenestrations (not shown) that allow the irrigation fluid to exit the balloon. These fenestrations are typically 0.025-0.500 millimeters in diameter.

Ablation module 78 is configured to monitor and control ablation parameters such as the level and the duration of ablation power (e.g., radio-frequency energy) conveyed to elongated electrodes 74 via I/O interface 56.

In the configuration shown in FIG. 2, balloon 72 comprises elongated electrodes 74 that are disposed longitudinally on the exterior surface of the balloon, and the balloon is affixed to a tubular shaft 90. Balloon 72 is configured to extend from a distal end of a lumen 92 of insertion tube 30, and the balloon can be deployed through the lumen into a body cavity such as heart 28. For simplicity, connections of elongated electrodes 74 to I/O interface 56 and ablation module 78 are not shown. In some embodiments, the connections are made by wires (not shown) running from the inside of the balloon to the outer surface of the balloon. The electrical connections can be formed with conductive epoxy or welding.

Elongated electrodes 74 can be fabricated with the balloon and typically comprise gold overlaying the exterior wall of balloon 72. In embodiments of the present invention, the elongated electrodes have respective lengths 94 that are at least twice as long as their respective widths 96.

As shown in FIG. 3, medical probe 22 also comprises an extender shaft 100 that is contained within tubular shaft 90, and is coupled to a distal end 102 of balloon 72. In operation, medical professional 34 can control a length 104 of balloon 72 (i.e., once the balloon is deployed from the lumen) by extending or retracting extender shaft 100 and the operator can control a width 106 of the balloon by specifying, to irrigation module 76, the flow rate of the irrigation fluid into the balloon.

In the configuration shown in FIG. 3, a magnetic field sensor 108 that is affixed to extender shaft 100 acts as a position transducer. In operation, processor 52 can process signals received from magnetic field sensor 108 in order to determine, in coordinate system 38, location coordinates of the magnetic field sensor. In some embodiments, as described hereinbelow, processor 52 can determine the current shape of balloon 72 (e.g., length 104 and width 106) based on the determined location coordinates that indicate the length of the balloon and the irrigation fluid flow rate that (i.e., combined with the current length of the balloon) indicates the current width of the balloon.

As shown in FIG. 3, Balloon 72 has a generally spherical shape when inflated. During a medical procedure, medical professional 34 may maneuver distal end 26 so that balloon 72 engages tissue 110 in a body cavity (e.g., heart 28) of patient 36. Balloon 72 can typically retain its generally spherical shape (and not have any distortion in the generally spherical shape) if a force 112 of the irrigation fluid on an inside surface 114 of the balloon is equal to or greater than a force 116 of tissue 110 on an outer surface 118 of the balloon.

In embodiments described hereinbelow, tissue 110 can be differentiated by appending a letter to the identifying numeral, so that the tissue comprises cardiac tissue 110A in heart 28, ostial tissue 110B in a pulmonary vein ostia 120, and intravenous tissue 110C in a pulmonary vein 122.

While the configuration of medical probe 22 presented in FIGS. 1-3 shows the medical probe comprising a balloon catheter having elongated electrodes 74 mounted on balloon 72, using any other type of medical probe 22 comprising any number of elongated electrodes configured to engage tissue in any body cavity in patient 36 is considered to be within the spirit and scope of the present invention.

Figure 4:
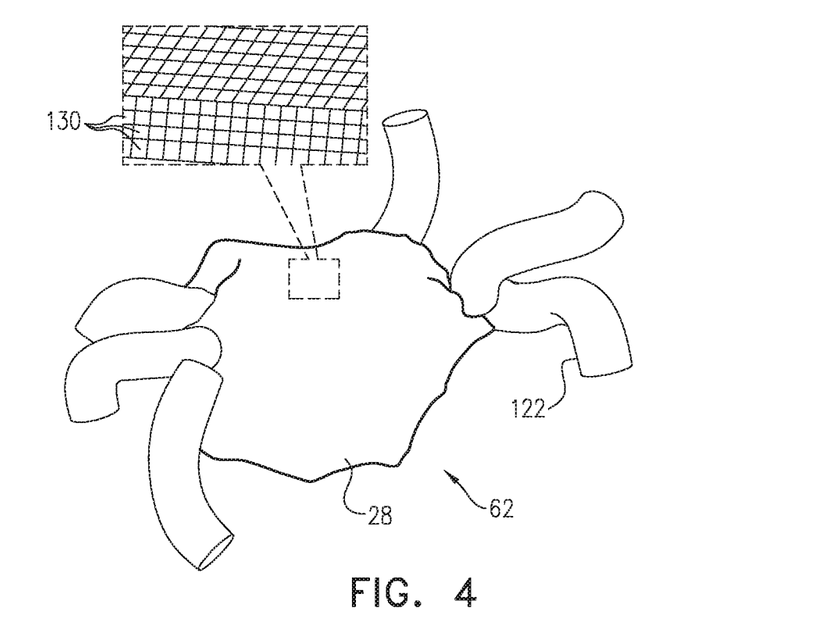
FIG. 4 is a schematic pictorial illustration of voxels that can be used to generate a 3D model of the body cavity, in accordance with an embodiment of the present invention.

FIG. 4 is a schematic pictorial illustration of voxels 130 that processor 52 can use to generate 3D model 58 of heart 28, in accordance with an embodiment of the present invention. In embodiments described herein, voxels 130 correspond to three-dimensional data points within tissue 110.

To generate model 58, processor 52 receives three-dimensional data for tissue 110, and then segments the received three-dimensional data into a set of voxels 130, wherein each given voxel 130 corresponds to a respective set of 3D location coordinates in coordinate system 38. As described supra, examples of the 3D data include anatomical mapping data received from a mapping catheter, computed tomography (CT) data, magnetic resonance imaging (MRI) data and ultrasound data.

Figure 5:
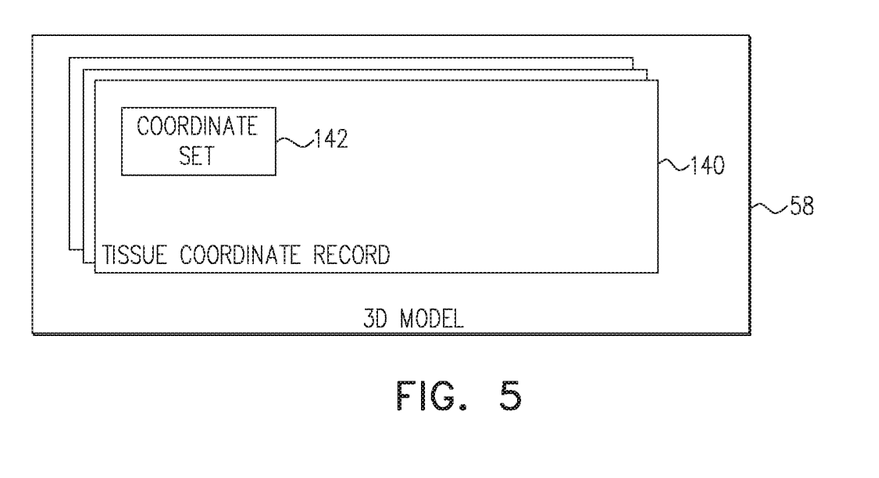
FIG. 5 is a block diagram showing an example of the 3D model of the body cavity, in accordance with an embodiment of the present invention.

FIG. 5 is a block diagram showing an example of 3D model 58, in accordance with an embodiment of the present invention. In the example shown in FIG. 5, model 58 comprises a plurality of tissue coordinate records 140 having a one-to-one correspondence with voxels 130. Each given record 140 comprises a set of 3D coordinates (i.e., in coordinate system 38) 142 for the corresponding voxel 130.

Figure 6:
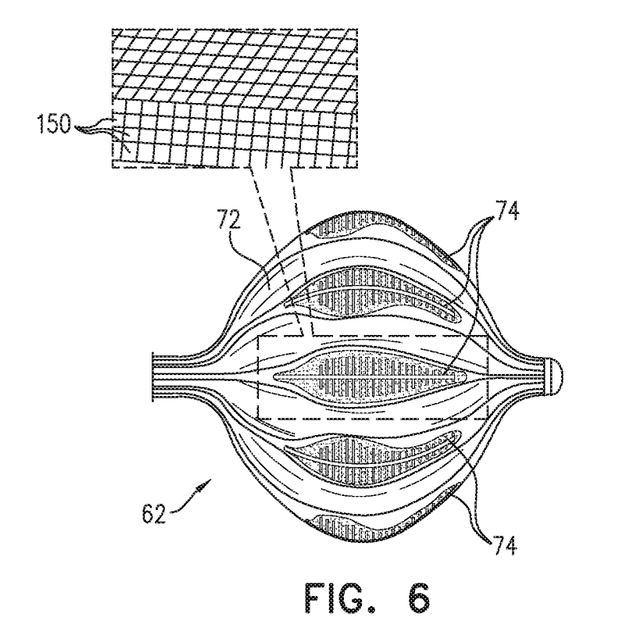
FIG. 6 is a schematic pictorial illustration of voxels that can be used to generate a 3D model of the balloon, in accordance with an embodiment of the present invention.

FIG. 6 is a schematic pictorial illustration of voxels 150 that processor 52 can use to generate 3D model 60 of heart balloon 72, in accordance with an embodiment of the present invention. In embodiments described herein, voxels 150 correspond to three-dimensional data points within balloon 72 and elongated electrodes 74.

Figure 7:
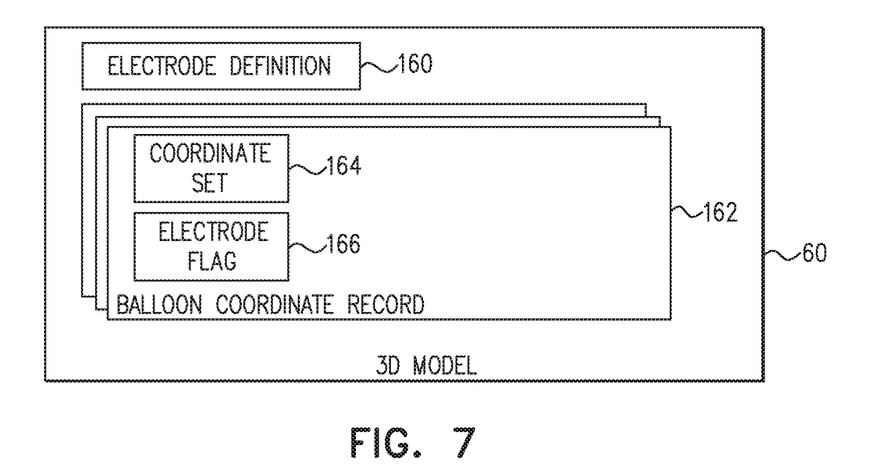
FIG. 7 is a block diagram showing an example of the 3D model of the balloon, in accordance with an embodiment of the present invention.

FIG. 7 is an example of 3D model 60, in accordance with an embodiment of the present invention. In the example shown in FIG. 7, model 60 comprises an electrode definition 160 and a plurality of balloon coordinate records 162 having a one-to-one correspondence with voxels 150. In some embodiments, electrode definition 160 comprises dimensions of electrodes 74.

Each given record 162 comprises a set of 3D coordinates (i.e., in coordinate system 38) 164 for the corresponding voxel 150, and an electrode flag 166. In some embodiments, processor can set electrode flag 166 (e.g., to "True") in a given record 162 if electrode definition 160 indicates that coordinates 164 in the given record correspond to the coordinates of a given elongated electrode 74.

When balloon 72 is inflated, the location coordinates that processor 52 computes for a given elongated electrode 74 (i.e., based on impedances and/or currents between adhesive skin patches 82 and the given elongated electrode) may comprise the location coordinates of a centroid of the given electrode. The centroid is herein assumed to be on the equator of balloon 72.

As described supra, balloon 72 has a generally spherical shape when inflated. Therefore, processor can use the location coordinates of the centroids of elongated electrodes to "model" balloon 72 so as to identify which voxels 150 correspond to the balloon, as described hereinbelow. In some embodiments, processor 52 can identify which voxels 150 correspond to elongated electrodes 74 based on the location coordinates of the centroids of the electrodes and electrode definition 160.

Figure 8:
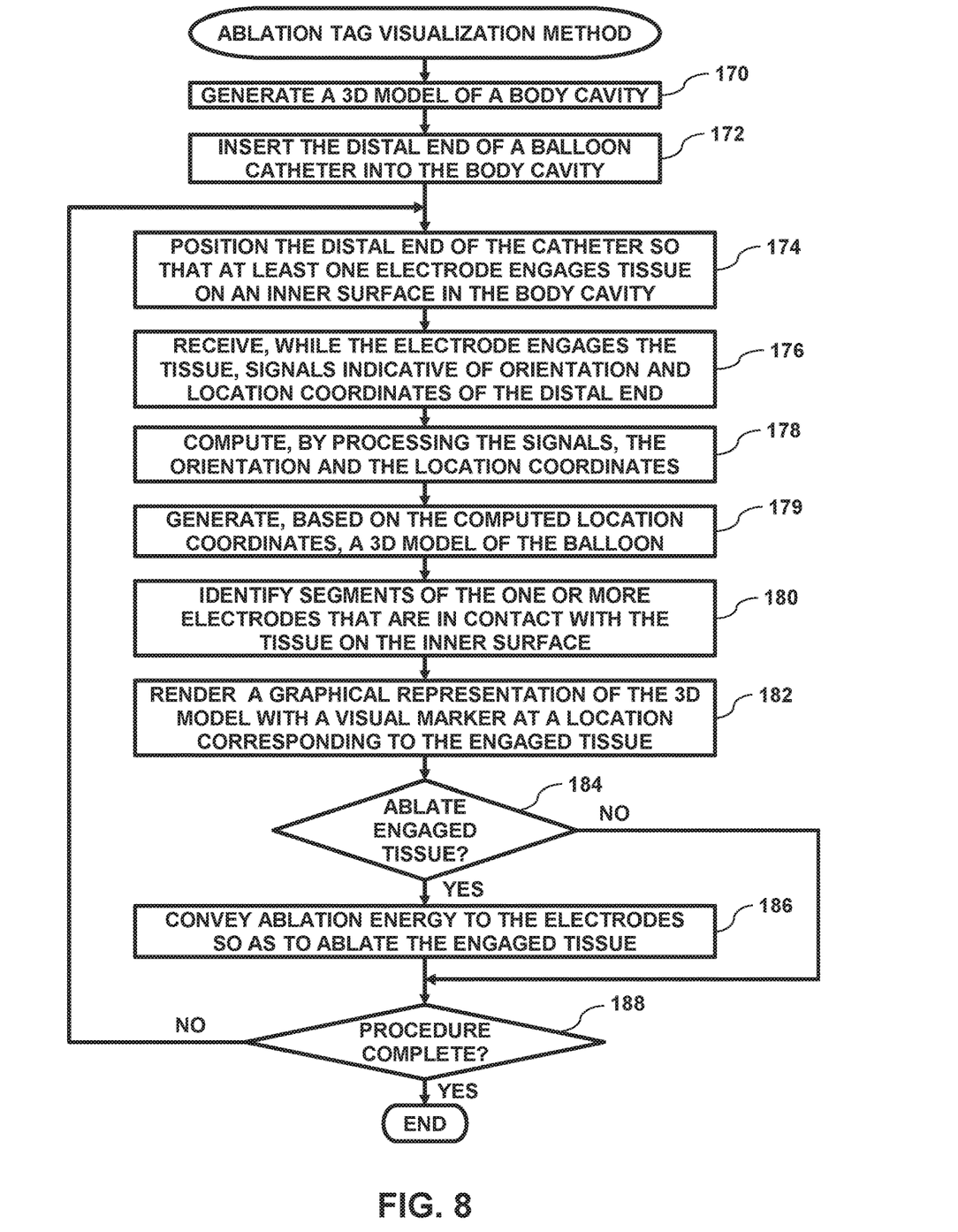
FIG. 8 is a flow diagram that schematically illustrates a method of presenting, on the 3D model of the body cavity, visual markers that correspond to engagement areas where the elongated electrodes engage tissue in the body cavity, in accordance with an embodiment of the present invention.
Figure 9:
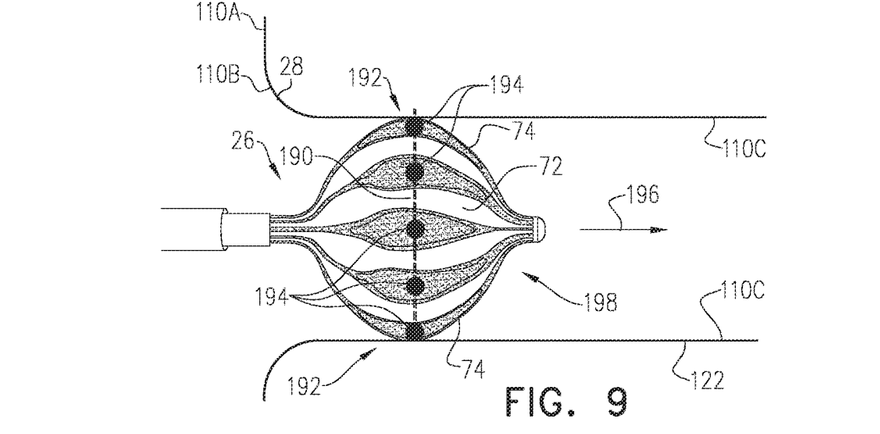
FIGS. 9-11 are schematic pictorial illustrations showing examples of the elongated electrodes engaging tissue in the body cavity, in accordance with an embodiment of the present invention.
Figure 10:
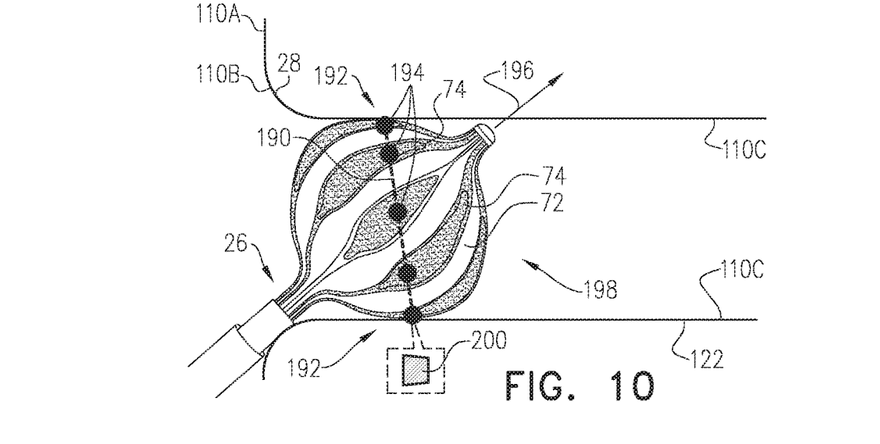
Figure 11:
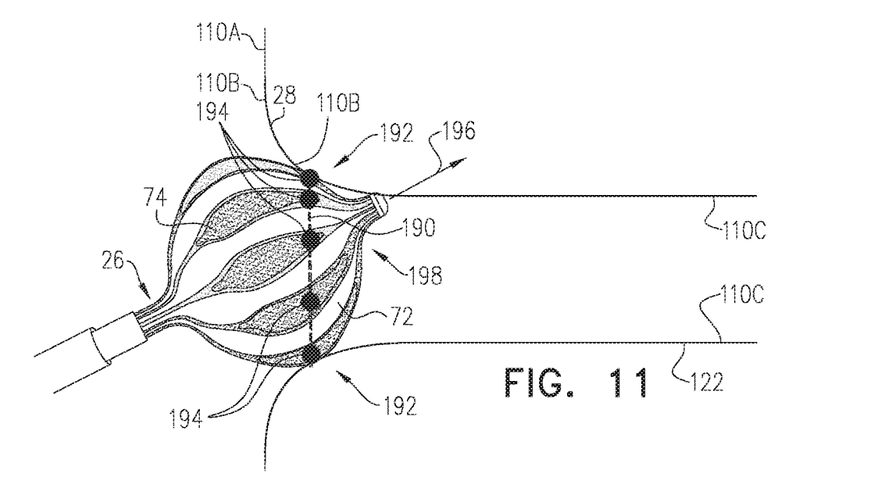

FIG. 8 is a flow diagram that schematically illustrates a method of presenting, on display 64, visual markers that correspond to location coordinates where elongated electrodes 74 engage an inner surface (i.e., tissue) in a body cavity such as heart 28, in accordance with an embodiment of the present invention. In a first model generation step 170, processor 52 generates 3D model 58. For example, processor 52 can generate 3D model 58 of a body cavity such as heart 28 or a pulmonary vein (as shown in FIGS. 9-11 and described hereinbelow) based on mapping points previously acquired by a mapping catheter (not shown). In some embodiments, processor 52 can augment (and increase the accuracy) of 3D model 58 with 3D image data received from a 3D imaging system such as a computed tomography (CT) scanner, a magnetic resonance imaging (MRI) scanner, or an ultrasound scanner.

In an insertion step 172, medical professional 34 inserts distal end 26 of medical probe 22 into the body cavity. Upon inserting distal end into the body cavity, the medical professional can inflate balloon 72 using methods described hereinabove.

In a positioning step 174, the medical professional manipulates handle 32 so that one or more elongated electrodes 74 engage tissue (e.g., tissue 110) on an inner surface of the body cavity. For example, medical professional can position distal end 26 so that at least one elongated electrode 74 engages tissue 110A in heart 28.

In a receive step 176, processor 52 receives, from position transducer 50, signals indicative of an orientation 196 and location coordinates 198 of distal end 26, and in a computation step 178, the processor computes the orientation and the location coordinates (i.e., in coordinate system 38) of the distal end. In a first location computation embodiment, magnetic field sensor 108 conveys, to processor 52, electrical signals in response to the magnetic fields generated by the coils in field generators 48, and upon receiving the electrical signals, the processor can compute a position (i.e., location coordinates and an orientation) of the magnetic field sensor (and thereby the position of distal end 26) within the body cavity.

In a second location computation embodiment, processor 52 determines location coordinates of distal end 26 inside the body cavity based on impedances and/or currents measured between adhesive skin patches 82 and elongated electrodes 74. As described supra, elongated electrodes 74 are disposed longitudinally on the exterior surface of balloon 72. When balloon 72 is inflated, processor 52 can compute (as described supra) the 3D location coordinates for each given elongated electrode 74 as a centroid of the given electrode. In some embodiments, processor 52 can compute an orientation of distal end 26 based on the 3D location coordinates of electrodes 74.

In a second model generation step 179, processor 52 generates model 60 for balloon 72. Since balloon 72 has a generally spherical shape when inflated and elongated electrodes 74 are disposed on the outer surface of the balloon, processor can compute a center of balloon 72 as an average of the location coordinates corresponding to the respective centroids of elongated electrodes 74, and then compute a radius of the balloon based on the computed center and the location coordinates of the electrodes. Using the computed radius and center, processor 52 can then compute sets of 3D location coordinates for balloon 72 in coordinate system 38, segment the computed sets of 3D location coordinates into a set of voxels 150, and store, to the respective balloon coordinate record 162 for each given voxel 150, the computed 3D location coordinates to coordinates 164.

As described supra, distal end comprises balloon 72 and elongated electrodes 74. Based on the location coordinates for the centroids of elongated electrodes 74 and the dimension information stored in electrode definition 160, processor 52 can compute sets of 3D location coordinates for the electrodes, and set the electrode flags in the balloon coordinate records whose coordinates 164 match any of the computed sets of 3D location coordinates for the electrodes. In other words, processor 52 can identify which voxels 150 correspond to the 3D location coordinates of the elongated electrodes.

FIGS. 9-11 are schematic pictorial illustrations showing examples of elongated electrodes engaging tissue on an inner surface of a body cavity such as heart 28, in accordance with an embodiment of the present invention. As shown in FIGS. 9 and 10, medical professional 34 inserts, via a chamber of heart 28, distal end 26 of medical probe 22 into pulmonary vein 122. Upon inserting balloon 72 into pulmonary vein 122 and extending extender shaft 100 into the pulmonary vein, medical professional 34 inflates (i.e., via irrigation module 76) balloon 72 so that respective segments 192 of one or more elongated electrodes 74 engage intravenous tissue 110C at respective engagement areas 194 (also referred to herein as sites), having respective contours 200, as shown in FIG. 10.

While a given elongated electrode 74 engages intravenous tissue 110C (or any other tissue 110 in a body cavity in patient 36), a given segment 192 of the given elongated electrode engages (i.e., is in contact with) the intravenous tissue at a given engagement area 194 on the intravenous tissue, while parts of the given elongated electrode other than the identified segment are not in contact with the intravenous tissue. In an identification step 180, processor 52 identifies respective segments 192 of the elongated electrodes engaging engagement areas 194 on the intravenous tissue.

In one embodiment, processor 52 can detect engagement areas 194 based on models 58 and 60. In this embodiment, processor 52 can use a collision detection algorithm on coordinate sets 142 and 164 to identify which voxels 150 are within a minimum distance threshold to any voxel 130. The identified voxels correspond to the location coordinates for engagement areas 194.

In the examples shown in FIGS. 9 and 10, medical professional 34 inserted distal end 26 into pulmonary vein 122 at different respective orientations 196. Due to the different orientations 196, the segment of a given elongated electrode 74 that engages intravenous tissue 110C in the example shown in FIG. 9 typically differs from the segment of the given elongated electrode that engages the intravenous tissue in the example shown in FIG. 10.

In some embodiments, as described hereinbelow, medical professional can instruct ablation module 78 to deliver ablation energy to elongated electrodes 74, thereby ablating intravenous tissue at engagement areas 194. In these embodiments, a line 190 connecting all engagement areas 194 may also be referred to as ablation line 190.

While the examples in FIGS. 9 and 10 show balloon 72 deployed in pulmonary vein 122, deploying the balloon in other organs of patient 36 and determining the locations of any tissue engaged by elongated electrodes 74 is considered to be within the spirit and scope of the present invention. For example, FIG. 11 shows segments 192 of elongated electrodes 74 engaging ostial tissue 110B at respective engagement areas 194.

Returning to the flow diagram, in a rendering step 182, processor 52 renders, to display 64, graphical representation 62 of 3D model 58, with visual markers at respective locations in the 3D model corresponding to the engagement areas on intravenous tissue 110C. In some embodiments (as shown in FIGS. 13 and 14 and described hereinbelow), processor 52 can render the visual markers using display contours corresponding to contours 200 of engagement areas 194.

Figure 12:
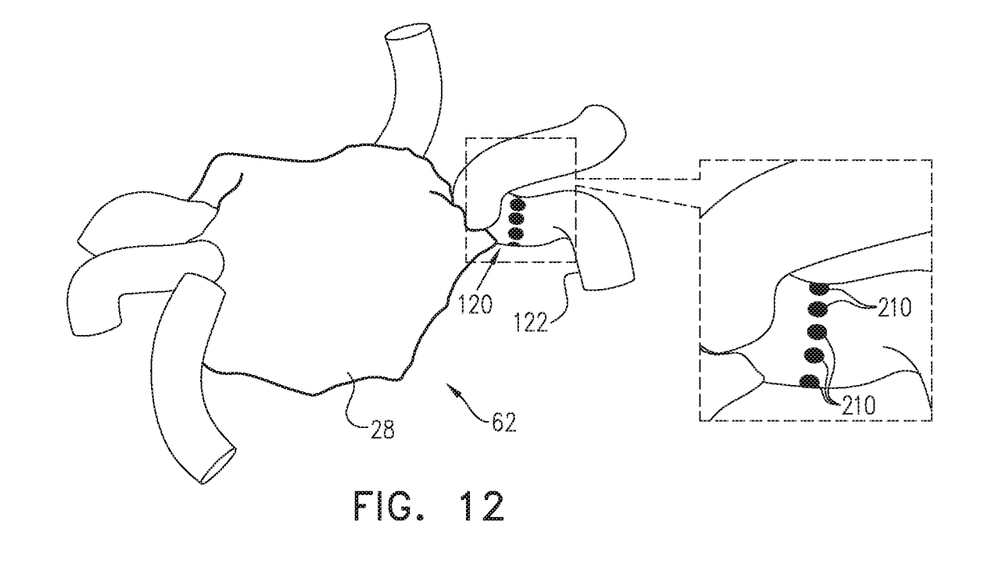
FIG. 12 is a schematic pictorial illustration of a graphical representation of the 3D model and the visual markers, in accordance with a first embodiment of the present invention.

FIG. 12 is a schematic pictorial illustration of graphical representation 62 of 3D model 58 representing heart 28, in accordance with a first embodiment of the present invention. In the first embodiment presented in FIG. 12, processor 52 renders graphical representation 62 with visual markers 210 that have circular display contours and correspond to engagement areas 194 on intravenous tissue 110C. While the example in FIG. 12 shows processor 52 rendering visual markers 210 as circular display contours, presenting the visual markers using other contours is considered to be within the spirit and scope of the present invention.

Figure 13:
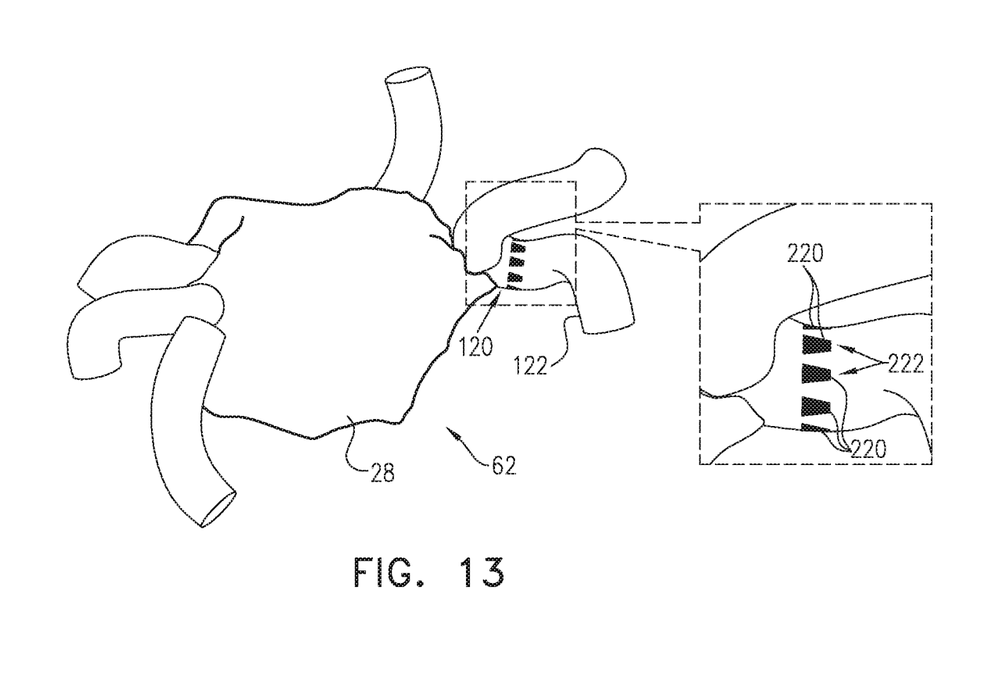
FIG. 13 is a schematic pictorial illustration of the graphical representation of the 3D model and the visual markers, in accordance with a second embodiment of the present invention.
Figure 14:
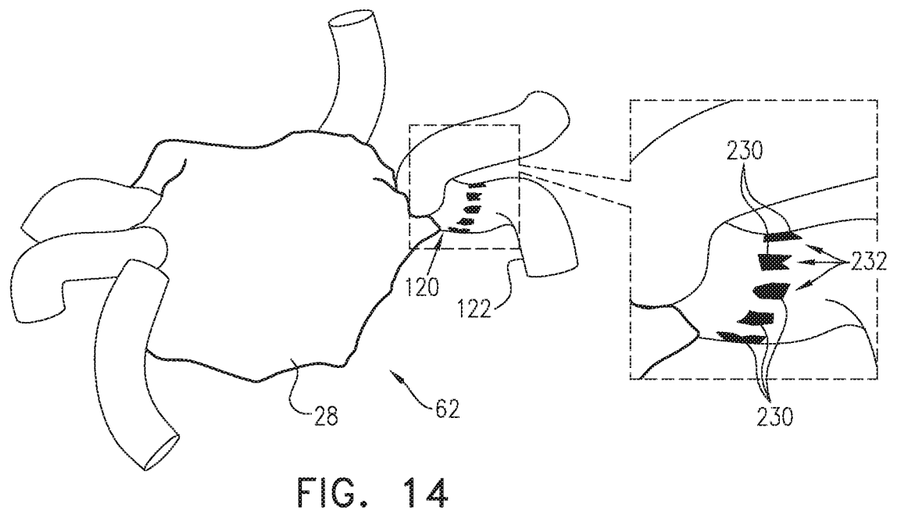
FIG. 14 is a schematic pictorial illustration of the graphical representation of the 3D model and the visual markers, in accordance with a third embodiment of the present invention.

FIG. 13 is a schematic pictorial illustration of graphical representation 62 of 3D model 58 representing heart 28, in accordance with a second embodiment of the present invention. In the second embodiment presented in FIG. 13, processor 52 renders graphical representation 62 with visual markers 220 that have trapezoidal contours 222 that are similar to contours 200 of their corresponding engagement areas 194.

The examples shown in FIGS. 12 and 13 correspond to orientation 196 of distal end 26 shown in FIG. 9 where the orientation of balloon 72 at the distal end is aligned with pulmonary vein 122. In some embodiments, the orientation of distal end 26 can be considered to be aligned with pulmonary vein 122 when orientation 196 is within 15 degrees of parallel with a section of the pulmonary vein comprising engagement area(s) 194. When balloon 72 is aligned with pulmonary vein 122, visual markers 220 may have similar contours 222, as shown in FIG. 13.

FIG. 14 is a schematic pictorial illustration of graphical representation 62 of 3D model 58 representing heart 28, in accordance with a third embodiment of the present invention. The example shown in FIG. 14 corresponds to orientation 196 of distal end 26 shown in FIG. 10, where the orientation of balloon 72 at the distal end is not aligned with pulmonary vein 122. When balloon 72 is not aligned with pulmonary vein 122, processor 52 can generate visual markers 230 that have differing contours 232 corresponding to contours 200 of their respective engagement areas 194, as shown in the third embodiment.

Returning to the flow diagram, in a first decision step 184, if the engaged intravenous tissue comprises intravenous tissue 110C targeted for ablation, then in an ablation step 186, ablation module 78 conveys ablation energy to elongated electrodes 74, thereby ablating the intravenous tissue engaged by the elongated electrodes. In some embodiments, ablation module 78 can convey ablation energy to elongated electrodes 74 in response to input received from medical professional 34 (e.g., via input devices 66).

In some embodiments, processor 52 can render each given visual marker 210, 220 or 230 in response to ablation module 78 delivering ablation energy to elongated electrodes 74. In these embodiments, the visual markers comprise ablation tags that indicate ablation locations on intravenous tissue 110C.

In a second decision step 188, if the medical procedure is not complete, then the method continues with step 174. If the medical procedure is complete, then the method ends.

Returning to step 184, if the engaged intravenous tissue does not comprise intravenous tissue 110C targeted for ablation, then the method continues with step 188.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An apparatus, comprising:
an invasive medical probe configured to be inserted into a body cavity and comprising a distal end having at least one elongated electrode disposed along the distal end;
a position transducer associated with the medical probe;
a memory configured to store a three-dimensional (3D) model of the body cavity;
a display; and
a processor configured:
to receive, from the position transducer, signals indicative of orientation and location coordinates of the distal end within the body cavity,
to identify, based on the 3D model and the signals, a segment along a length of a given elongated electrode that is in contact with tissue at a site on an inner surface of the body cavity, while parts of the given elongated electrode other than the identified segment are not in contact with the inner surface of the body cavity,
to determine, based on the 3D model and the signals, an engagement contour of the segment along the length of the given elongated electrode that is in contact with the tissue, the engagement contour being indicative of an alignment between the distal end and the site, and
to render to the display a graphical representation of the 3D model with a visual marker contour at a location on the 3D model corresponding to the engagement contour and to the site contacted by the segment of the given elongated electrode.

2. The apparatus according to claim 1, wherein the at least one elongated electrode is disposed longitudinally along the distal end of the medical probe and comprises a width and a length that is at least twice as long as the width.

3. The apparatus according to claim 1, and comprising an inflatable balloon that extends from a lumen in the distal end of the medical probe.

4. The apparatus according to claim 3, wherein the at least one elongated electrode is disposed longitudinally on a surface of the balloon and comprises a width and a length that is at least twice as long as the width.

5. The apparatus according to claim 1, and further comprising an ablation module configured to deliver ablation energy to the at least one elongated electrode, thereby ablating the tissue that is in contact with the at least one electrode.

6. The apparatus according to claim 5, wherein the visual marker corresponds to the site ablated by the segment of the given elongated electrode.

7. The apparatus according to claim 1, wherein the processor is further configured, to receive, prior to receiving the signals, 3D model data for the body cavity, and to generate, using the 3D model data, the 3D model.

8. The apparatus according to claim 7, wherein the 3D model data is selected from a list consisting of anatomical mapping data, computed tomography data, magnetic resonance imaging data and ultrasound data.

9. The apparatus of claim 1, the visual marker contour comprising:
a first contour when the distal end and the tissue are aligned; and
a second contour, different from the first contour, when the distal end and the tissue are not aligned.

10. A method, comprising:
generating a three-dimensional (3D) model of a body cavity;
receiving, from a position transducer associated with a medical probe configured to be inserted into the body cavity and comprising a distal end having at least one elongated electrode disposed along the distal end, signals indicative of orientation and location coordinates of the distal end within the body cavity;
identifying, based on the 3D model and the signals, a segment along a length of a given elongated electrode that is in contact with tissue at a site on an inner surface of the body cavity, while parts of the given elongated electrode other than the identified segment are not in contact with the inner surface of the body cavity;

determining, based on the 3D model and the signals, an engagement contour of the segment along the length of the given elongated electrode that is in contact with the tissue, the engagement contour being indicative of an alignment between the distal end and the site; and rendering to the display a graphical representation of the 3D model with a visual marker contour at a location on the 3D model corresponding to the engagement contour and to the site contacted by the segment of the given elongated electrode.

11. The method according to claim 10, wherein the at least one elongated electrode is disposed longitudinally along the distal end of the medical probe and comprises a width and a length that is at least twice as long as the width.

12. The method according to claim 10, wherein the medical probe comprises an inflatable balloon that extends from a lumen in the distal end of the medical probe.

13. The method according to claim 12, wherein the at least one elongated electrode is disposed longitudinally on a surface of the balloon and comprises a width and a length that is at least twice as long as the width.

14. The method according to claim 10, and further comprising delivering, by an ablation module, ablation energy to the at least one elongated electrodes, thereby ablating the tissue that is in contact with the at least one electrode.

15. The method according to claim 14, wherein the visual marker corresponds to the site ablated by the segment of the given elongated electrode.

16. The method according to claim 10, and comprising receiving, prior to receiving the signals, 3D model data for the body cavity, and to generate, using the 3D model data, the 3D model.

17. The method according to claim 16, wherein the 3D model data is selected from a list consisting of anatomical mapping data, computed tomography data, magnetic resonance imaging data and ultrasound data.

18. The method of claim 10, the visual marker contour comprising:
  a first contour when the distal end and the tissue are aligned; and
  a second contour, different from the first contour, when the distal end and the tissue are not aligned.

19. A computer software product, operated in conjunction with a medical probe configured to be inserted into a body cavity and comprising a distal end having at least one elongated electrode disposed along the distal end, the product comprising a non-transitory computer-readable medium, in which program instructions are stored, which instructions, when read by a computer, cause the computer:
  to generate a three-dimensional (3D) model of a body cavity;
  to receive, from a position transducer associated with the medical probe, signals indicative of orientation and location coordinates of the distal end within the body cavity;
  to identify, based on the 3D model and the signals, a segment along a length of a given elongated electrode that is in contact with tissue at a site on an inner surface of the body cavity, while parts of the given elongated electrode other than the identified segment are not in contact with the inner surface of the body cavity;
  to determine, based on the 3D model and the signals, an engagement contour of the segment along the length of the given elongated electrode that is in contact with the tissue, the engagement contour being indicative of an alignment between the distal end and the site; and
  to render to the display a graphical representation of the 3D model with a visual marker contour at a location on the 3D model corresponding to the engagement contour and to the site contacted by the segment of the given elongated electrode.

20. The computer software product of claim 19, the visual marker contour comprising:
  a first contour when the distal end and the tissue are aligned; and
  a second contour, different from the first contour, when the distal end and the tissue are not aligned.

* * * * *